US006573107B1

(12) United States Patent
Bowen et al.

(10) Patent No.: US 6,573,107 B1
(45) Date of Patent: Jun. 3, 2003

(54) IMMUNOCHEMICAL DETECTION OF AN EXPLOSIVE SUBSTANCE IN THE GAS PHASE THROUGH SURFACE PLASMON RESONANCE SPECTROSCOPY

(75) Inventors: John M. Bowen, Laramie, WY (US); Lewis J. Noe, Laramie, WY (US); B. Patrick Sullivan, Laramie, WY (US)

(73) Assignee: The University of Wyoming, Laramie, WY (US)

( * ) Notice: Subject to any disclaimer, the term of this patent is extended or adjusted under 35 U.S.C. 154(b) by 0 days.

(21) Appl. No.: 09/259,810

(22) Filed: Feb. 26, 1999

Related U.S. Application Data (60) Provisional application No. 60/095,389, filed on Aug. 5, 1998.

(51) Int. Cl.[7] .............................................. G01N 33/543
(52) U.S. Cl. ...................... 436/518; 356/317; 356/318; 356/244; 422/57; 422/82.05; 422/82.11; 422/83; 422/93; 435/287.1; 435/287.2; 435/288.3; 435/288.7; 435/807; 435/808; 436/164; 436/165; 436/524; 436/525; 436/527; 436/805
(58) Field of Search ................................. 356/317, 318, 356/244; 422/57, 82.05, 82.11, 83, 93; 435/287.1, 287.2, 288.3, 288.7, 807, 808; 436/164, 165, 518, 524, 525, 527, 805

(56) References Cited

U.S. PATENT DOCUMENTS

| RE30,627 E | 5/1981 | Bagshawe et al. ......... 23/230 R |
|---|---|---|
| 4,844,613 A | 7/1989 | Batchelder et al. .......... 356/318 |
| 4,857,273 A | 8/1989 | Stewart ........................ 422/68 |
| 4,877,747 A | 10/1989 | Stewart ....................... 436/525 |
| 4,978,503 A * | 12/1990 | Shanks et al. ................. 422/58 |
| 5,023,053 A | 6/1991 | Finlan ..................... 422/82.05 |
| 5,183,740 A * | 2/1993 | Ligler et al. ................ 435/7.32 |
| 5,242,828 A * | 9/1993 | Bergstrom et al. ........... 435/808 |
| 5,496,700 A | 3/1996 | Ligler et al. .................. 435/7.1 |
| 5,763,191 A * | 6/1998 | Knoll et al. .................. 435/7.1 |

OTHER PUBLICATIONS

Patel et al, "Immobilization of protein molecules onto homogeneous and mixed carboxylate terminated self assembled monolayers", Langmuir, 1997, 13(24), 6485–6490.*

Ligler, Frances S.; Anderson, George P.; Davidson, Peggy T.; Foch, J. Richard J.; Ives, Jeffrey T.; King, Keeley D.; Page, Greg; Stenger, David A.; Whelan, James P.; "Remote Sensing Using an Airborne Biosensor," Environmental science & technology; Aug. 15, 1998, v 32 n 16; p.: 2461, American Chemical Spociety.

Ngeh–Ngwainbi, Foley, J., Kuan, P. H., Guilbault, G. G., J. Am. Chem. Soc., 1986, 108,18, 5444–5447.

E. C. Hahn and G. G. Guilbault, Ph.D. Thesis, University of New Orleans, LA, 1988.

(List continued on next page.)

*Primary Examiner*—Christopher L. Chin
(74) *Attorney, Agent, or Firm*—Santangelo Law Offices, P.C.; Craig R. Miles (57) ABSTRACT

The biosensor involves a specially designed surface which can be optically coupled to a Surface Plasmon Resonance spectrometer. The key components of the biosensor are a bimetallic layer, a self assembled monolayer of chemicals and a layer of biomolecules such as special antibodies. The innovative bimetallic layer combines the sensitivity of silver metal and durability of gold and thus make it an ideal biosensor layer not only for a low volatility gas phase detection but also for a liquid phase detection. The successful application of the biosensor in high explosive substance detection proves that the biosensor is a sensitive and highly specific device for security and anti-terrorism applications, when it is combined with a Surface Plasmon Resonance Spectroscope.

30 Claims, 4 Drawing Sheets

OTHER PUBLICATIONS

Suleiman, A. A., Guilbault, G. G., Analyst, 1994, 119, 2279–2282.

Suleiman, A. A., Guilbault, G. G., Analytical Letters, 1991, 24, 1283–1291.

Attili, B. S., Suleman, A. A., Microchemical Journal, 54, 1996, 174–179.

Rouhi, A., C&EN, Mar. 10, 1997, 14–22.

Katerkamp, A., Bolsmann, P., Niggemann, M., Pellmann, M., Cammann, K., Mikrochim. Acta., 1995, 119, 63–72.

Ehler, T. T., Noe, L. J., Langmuir, 1995, 11, 4177–4179 John M. Bowen, Lewis J. Noe, B. Patrick Sullivan.

Ehler, T. T., Malmberg, N., Noe, L. J., J. Phys. Chem., 1997, 101, 1268–1272.

Whelan, J. P., Kusterbeck, A. W., Wemhoff, G. A., Bredehorst, R., Ligler, F. S., Anal. Chem. 1993, 65, 3561–3565.

Scott Paulson, Kevin Morris and B. Patrick Sullivan, A General Preparative Route to Self–assembled Monolayer Surfaces of Polypyridine Ligands and their Metal Complexes, Department of Chemistry, University of Wyoming, Laramie, WY 82071–3838, USA, pp. 1615–1617.

* cited by examiner

IMMUNOCHEMICAL DETECTION OF AN EXPLOSIVE SUBSTANCE IN THE GAS PHASE THROUGH SURFACE PLASMON RESONANCE SPECTROSCOPY

This application is a continuation application of a provisional application (Serial No. 60/095,389) filed on Aug. 5, 1998, which is hereby incorporated by reference.

I. BACKGROUND OF THE INVENTION

Generally, this invention relates to an apparatus for detection of a controlled substance via Surface Plasmon Resonance Spectroscopy (SPRS). Specifically, this invention relates to a new biosensor element to be used in combination with SPRS for immunochemical detection of an explosive substance for security and anti-terrorism purposes. This invention also relates to methods for using this biosensor element in combination with SPRS for the aforementioned purposes in different conditions such as a gas phase, a liquid phase or a solid phase (e.g., gel state).

Biosensors are becoming a reliable and economical method of analysis for compounds from the areas of environmental chemistry to medicine. These methods are selective due to the very specific nature of the antibody-antigen reaction and generally offer low limits of detectability. In most applications, though, these immuno-biosensors have been used primarily for solution based analyses. One example is a biosensor for the detection of TNT and RDX developed by the U.S. Naval Research Laboratory which purportedly can reliably detect these compounds in the concentration range of 20–1200 ppb (Ngeh-Ngwainbi et al., 1986, J. Am. Chem. Soc., 108,18: 5444–5447). This instrumental method purportedly utilized an aqueous competitive fluorescent tagged antigen competition scheme with fluorescence detection. Since these techniques are for the detection of explosives only in solution, their subsequent applications where detection of explosives in air is necessary are quite limited.

Although this work has been disputed, Gas Phase Immunoassay (GPI) was purportedly demonstrated by Guilbault in the vapor phase detection of cocaine and the insecticide parathion. In the Guibault effort, parathion was purportedly detected at 35 ppb in air, its saturated concentration, and the immunochemical reaction was purportedly found to be reversible and reproducible to within 6%. Response time was purportedly less than a minute with no preconcentration step. The antibody was also purportedly found to react with other related pesticides. However, since the reaction with pesticides only occurred at high pesticide concentrations, the assay was considered to be quite specific, or having minimal non-specific interactions at other than high concentrations. It was, however, subject to the limitations of the immunoassay method.

For such experiments, the antibodies for the respective compounds were immobilized onto a piezoelectric crystal by simply drying the protein onto the surface. This limited the number of antibody proteins available to undergo the antibody-antigen reaction since some receptors were buried under others (Ngeh-Ngwainbi et al., 1986, J. Am. Chem. Soc., 108,18: 5444–5447; Hahn and Guibault, 1988, Ph.D. thesis).

Due to the limitations of utilizing a gas phase immunoassay reaction, an improved method for detecting the reaction is needed. Unfortunately, few analytical methods have appeared to be applicable to the detection of the immunochemical reaction in the gas phase. In Guibault's method for the detection of cocaine and parathion, as in several others (Suleiman and Guibault, 1994, Analyst 119: 2279–2282; Suleiman and Guibault, 1991, Analytical Letter 24: 1283–1292; Attili and Suleiman, 1996, Microchemical Journal, 54: 174–179), the immunochemical receptor, the commercial antibody for parathion, for instance, was immobilized onto a piezoelectric crystal. The immunochemical chemical reaction was observed as a function of the change in the shear mode of the quartz crystal which changes due to mass loading of the analyte. This sensitive analytical method is termed the Quartz Micro Balance (QMB). The Bofors Applied Technologies method uses this detection method for their TNT biosensor (Rouhi, 1997, C&EN, March 10, 14–22).

This invention is based on a wholly different detection method using spectroscopy. This is Surface Plasmon Resonance Spectroscopy (SPRS) which is described in detail below.

SPRS has previously been used for a liquid phase, such as to detect the antibody-hapten reaction in liquids from the tip of an optical fiber probe. Katerknap, et al. (Acta., 1995, 119: 63–72) described the use of this form of spectroscopy which can purportedly detect the immunochemical interaction for bovine serum albumin (BSA)/anti-BSA at 0.2 ug/mL in solution. Ehler, et al. (Ehler and Noe, Langmuir, 1995, 11:4177; Ehler, Malmberg, Noe, 1997, J. Phys. Chem., 101:1268–1272) utilized a more traditional geometry for SPRS consisting of a glass slide with a sputtered metal surface interfaced onto a movable prism. By arranging a self assembled monolayer (SAM) on the surface of the slide, they were able to detect differences in the thickness and the calculated tilt angle of a self assembled monolayer on the metal surface with SPRS in the gas phase. For example, difference in the carbon chain length of two methyl units was easily detectable. Unfortunately, there has been a long felt, but unsatisfied need for a system that achieves the high specificity and low detection levels desired for security and other applications.

When a device such as an explosive detection system is designed for use, it needs to satisfy the common requirements for, first of all, specificity; second, simplicity; third, convenience; and fourth, speed. Some problems existing in this specific field are the complexity of the existing methods and equipments, and the inability of detection of an explosive or other controlled substance in a gas phase using a simple device. Substantial attempts by those skilled in the art to fill the need for a detection device that is simple, yet specific have not been successful, possibly because of failure to understand the nature of problems. In fact, previous art seems to teach away from the technical direction in which the patentee went. It is this invention that satisfies the need. A simple but effective biosensor element innovatorily advances the detection process and equipment needed when it is combined with a SPRS technology. From this perspective, this invention seems to represent not a just gradual slope of improvement but rather an innovative creation of a detection device and a new direction for such devices.

II. SUMMARY OF THE INVENTION

In view of the foregoing, it is a primary object of the present invention to provide an innovative biosensor element to be used in combination with SPRS for immunochemical detection of an explosive substance, such as for security and anti-terrorism purposes. The biosensor comprises a specially designed surface which can be optically coupled to a Surface Plasmon Resonance (SPR) spectrometer. The biosensor surface can be comprised of a substrate of the same material as the SPR optical component and can be metallized. A chemical layer consisting of a thiol can be reacted onto the surface as a Self Assembled Monolayer (SAM). Onto this reactive SAM, biomolecules such as antibodies, antibody fragments, proteins or other substances can be reacted with the SAM producing a biosensor surface which can be utilized in the detection process.

Thus, it is an object of this invention to provide a biosensor element for detection of a controlled substance via Surface Plasmon Resonance Spectroscopy (SPRS). The controlled substances may include, but not limited to, a highly explosive component, a drug or even an accelerant such as of interest in an arson investigation or the like.

It is also an object of this invention to provide a biosensor element for detection of a harmful biological agent in air via SPRS, such as anthrax spores, bacteria, fungal spores and viruses, for anti-biological weapon or air quality control and environmental pollution watch or the like.

It is still another object of this invention to provide a biosensor element for detection of a controlled substance in a liquid phase via SPRS such as a drug in a blood sample.

This invention also relates to methods for using this biosensor element in combination with SPRS for the aforementioned purposes in different conditions such as a gas phase, a liquid phase or a solid phase (e.g., including a gel state).

Naturally, further objects of the invention are disclosed throughout other areas of the specification, drawings, and claims.

IV. DETAILED DESCRIPTION OF THE PREFERRED EMBODIMENTS

Figure 1:
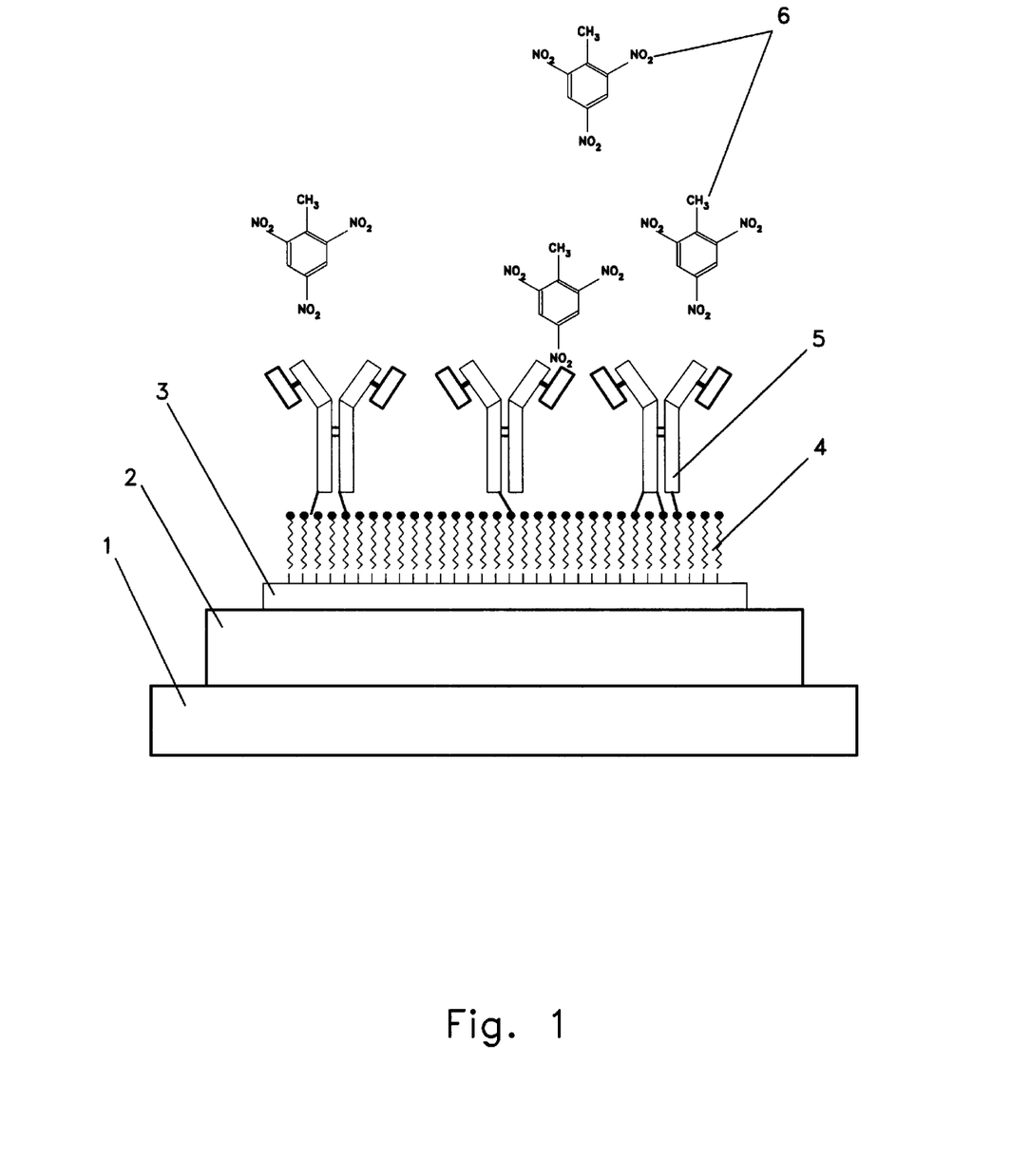
FIG. 1 is a schematic cross sectional view of an embodiment of the invention showing a biosensor element.
Figure 2:
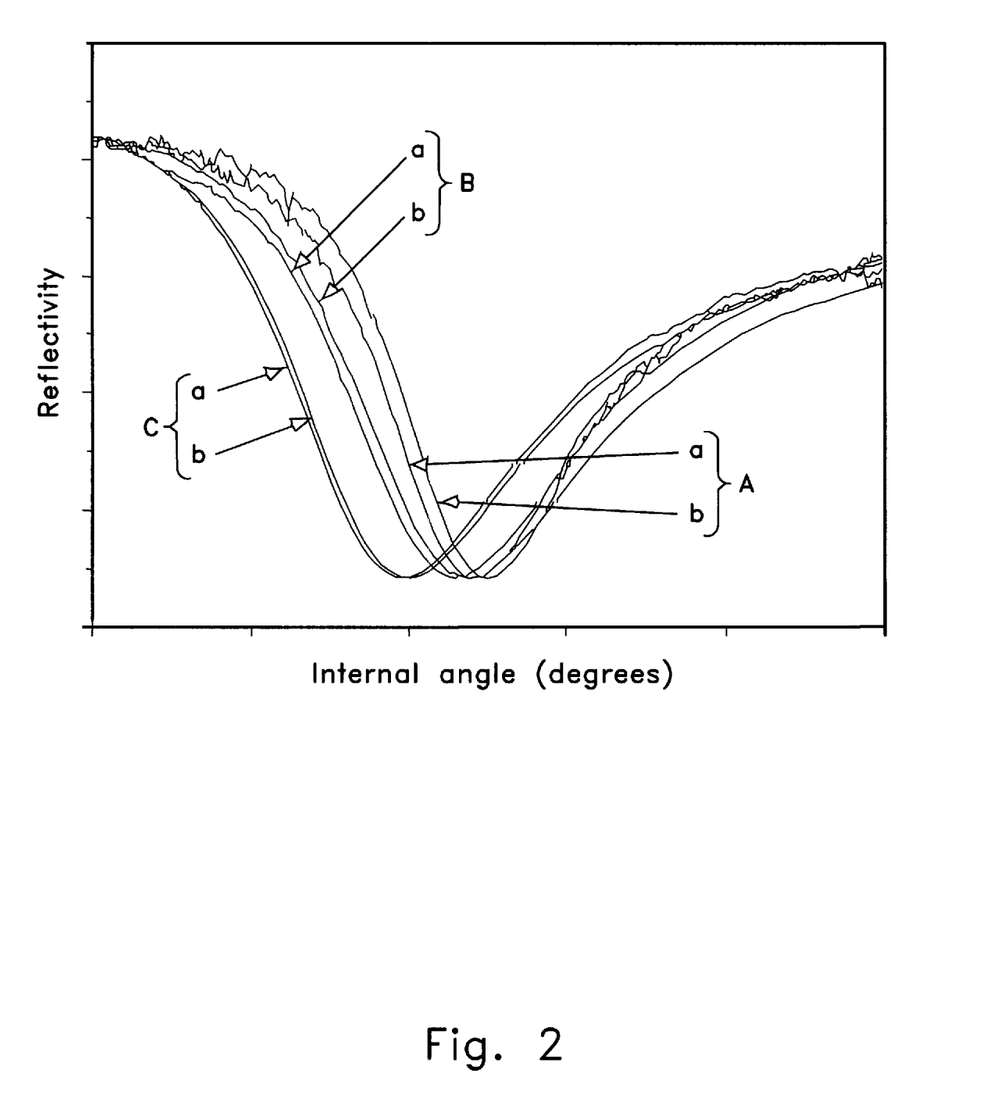
FIG. 2 is a plot showing SPR data for antibody dilution series for analysis of TNT vapor. These curves show antibody concentrations at 109 $\mu$g/ml (A), 54.2 $\mu$g/ml (B) and 27.3 $\mu$g/ml (C). The slides were later exposed to TNT vapor at 10 min intervals. These data indicate that the SPR curves irreversibly shift with the amount of antibody on the biosensor surface, and prove that the shift in the SPR curve is due to the gas phase immunochemical reaction. Letter "a" shows the curves before exposure and letter "b" shows the curves after exposure.

As can be understood, the basic concepts of the present invention may be embodied in many different ways. The present invention is an innovative biosensor element for use with Surface Plasmon Resonance Spectroscopy (SPRS) which is applicable for rapid and sensitive detection of analytes in both the liquid and gas phases. FIG. 1 shows the schematic drawing of the structure of the biosensor element. The biosensor element comprises a specially designed surface (2) which can be optically coupled to a Surface Plasmon Resonance (SPR) prism (1). The biosensor surface (2) can be comprised of a substrate of the same material as the SPR optical component. A metallized layer (3) can be coated on the substrate surface. A chemical layer (4) such as a thiol can be reacted onto the surface as a Self Assembled Monolayer (SAM). Onto this reactive SAM, biomolecules (5) such as antibodies, antibody fragments, or proteins can be reacted with the SAM producing a biosensor surface which can be utilized in the detection process to capture a substance of interest (6), such as a highly explosive substance or the like.

The SPR biosensor element can include a substrate surface covered by at least one layer of compounds. The substrate itself can be of the same material as the SPR optical dispersion device, or prism, such that the two components have matching indices of refraction. Naturally, the substrate can be optically coupled to the SPR prism.

One side of the substrate surface can be silianized using one of several methods, such as the method shown by Majda for use on glass (Analytical Chemistry, Volume 63, No 1, Jan. 1, 1991 or J. Chem. Soc., Chem. Commun., 1615–1617, 1992). The purpose of this layer (not shown) can be to stabilize the following layers.

Figure 3:
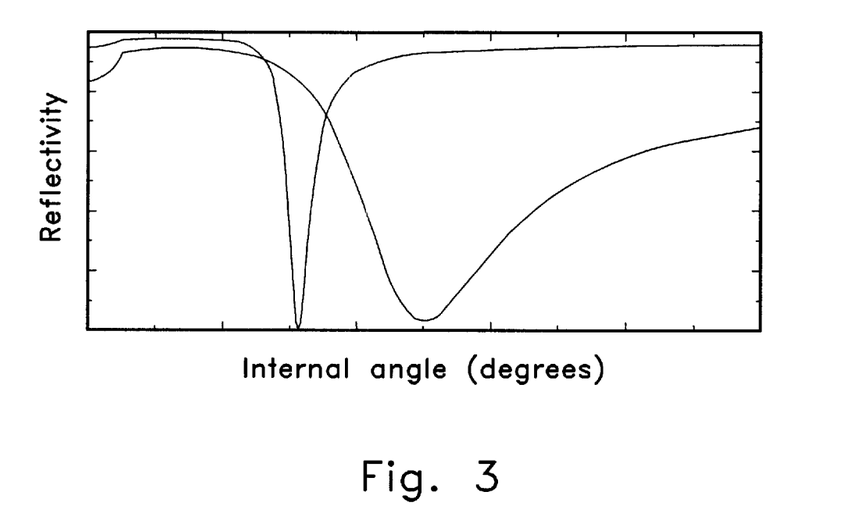
FIG. 3 is a plot showing surface plasmon curves of gold (Au) and silver (Ag) surfaces.
Figure 4:
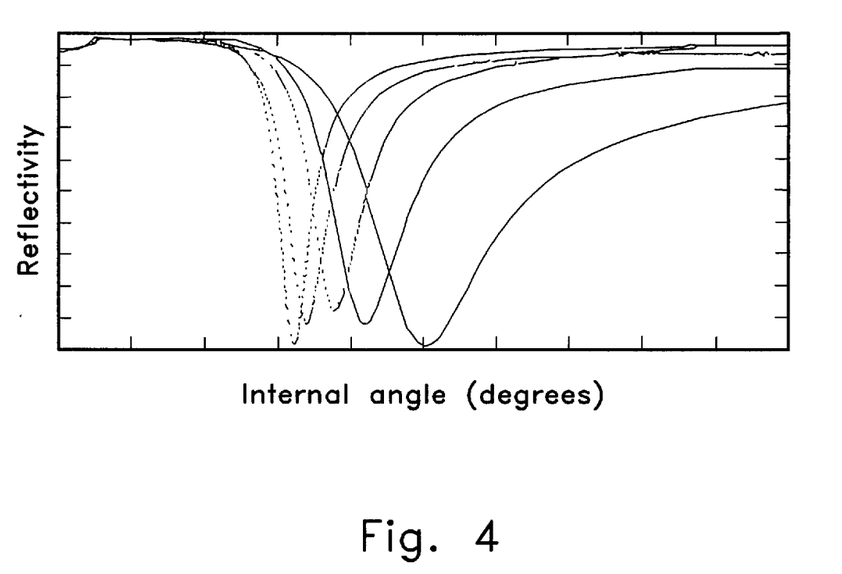
FIG. 4 is a plot showing experimental surface plasmon resonance curves which are as follows (starting at left): pure silver; 2:1 silver/gold; 1:2 silver/gold; pure gold.

After silanization, the surface can be coated with thin layers of silver and gold. Because of the inertness of gold, it appears to be the best choice for preparing dielectric films designed for biospecific plasmon analysis. However, as can be seen from FIG. 3, the plasmon spectrum of gold has a band width approximately three times the width of silver. Consequently, biospecific plasmon detection sensitivity is reduced for proteins attached to gold in comparison to silver, making gold based SPR surface less sensitive to shifts in thickness. These shifts are characterized by a displacement of the position of the plasmon curve in internal angle. Because of the above deficiency, we have developed Ag/Au bilayer films which narrow the plasmon curves while retaining the durability of the gold surface, as shown in FIG. 4.

The next layer of the surface can involve the reaction of an organic based "tether" which will react with both the metallized surface and with the proteinaceous biomolecule, which is the active portion of the biosensor surface. This "tether" layer can be reacted to the metalized surface as a Self Assembled Monolayer (SAM). The active biomolecule can be a complete antibody, either monoclonal or polyclonal depending on the application, an antibody fragment, or even a specialized protein or protein-like macro molecule which is sensitive to a specific analyte, among other choices. For simultaneous detection applications, two or multiple antibodies can be immobilized onto the tether for detection of two or multiple antigens of interest simultaneously. The term multiple used here refers to more than two antibodies or antigens.

Figure 5:
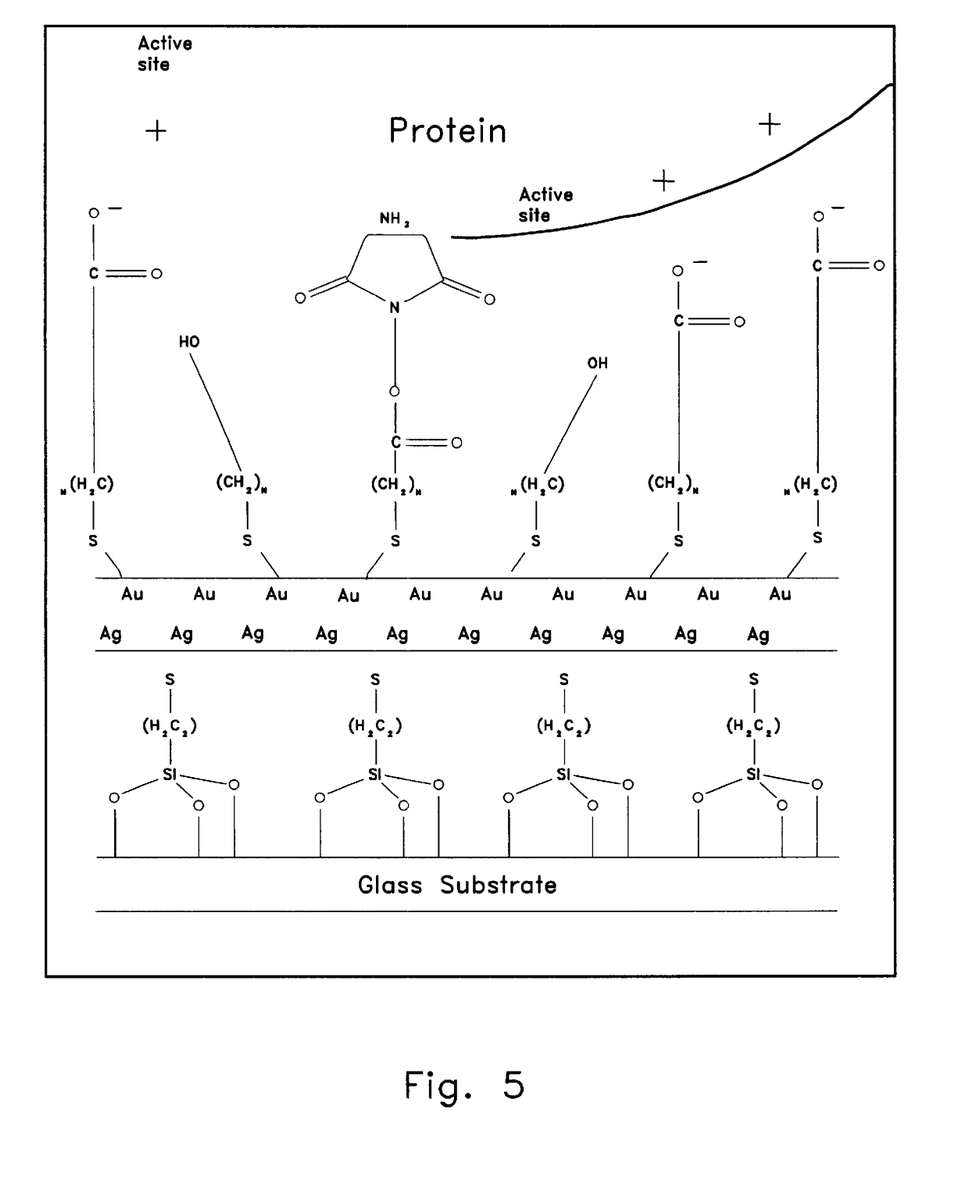
FIG. 5 is a schematic illustration showing the immobilization methods for the antibody onto the tether surface.

FIG. 5 illustrates the surface of the derivatized gold substrate slide before biomolecule immobilization. A biomolecule used here is a macro molecule such as a DNA, a RNA, a protein molecule, an antibody or one of the aforementioned antibody and protein fragments. Binding of the biomolecule can occur on reaction of a succinimide ester and the amine or other groups of the protein or active biomolecule surface forming amide linkages, —S—$(CH_2)_n$CONH-Protein. Succinimide esters that remain unreacted may or may not be quenched with ethanolamine, $H_2NCH_2CH_2OH$, hydrochloride at basic pH ~8.5 to give the amide, R—CONHCH$_2$CH$_2$OH. As a nonlimiting illustration, we have successfully utilized 11,11'dithio-bis (succinimidylundecanoate) in a solution of methylene chloride and methanol as the tether layer using a silianized glass substrate.

As mentioned, the active biomolecule can react with the SAM "tether" layer to form a SPR biosensor surface with the biomolecule arranged close to the metal plasmon surface allowing maximum sensitivity. As a non-limiting example, a monoclonal antibody in a phosphate buffer at pH 8.2 can be added to the SAM coated surface for any period, such as longer than two hours, to produce a workable surface. This surface has been successfully demonstrated in the analysis of TNT in the vapor and liquid phase.

A key factor in our antibody surface preparation lies in the fact that SAMs of alkane thiols, $HS(CH_2)_nCH_3$, or their carboxylic acid or alcohol derivatives will migrate on a Au surfaces. We believe this phenomenon of migration may minimize denaturation of the antibody when it covalently couples. This may allow the antibody tertiary structure to dictate the position of the immobilizing thiols such that "nestling in" can occur with the movement of properly derivatized alkane thiols of differing lengths. This process, which may take long periods of time to reach equilibrium, perhaps hours, is determined by the diffusional movement of derivatized alkane thiols bonded to the gold surface.

This process produces a stable, fast reacting and sensitive SPR based biosensor of wide applicability. It is substantially different from the use of other binding matrices utilizing large biological linking compounds such as streptavidin, or a direct antibody-metal surface interaction. Our formulation links the biomolecule to the metal surface without denaturing the protein and minimizes the alteration in the protein tertiary structure, which can be important in preserving binding site activity. This allows for rapid and very specific detection of compounds or analytes in air. All present biosensor technology involving SPRS seems to rely on a liquid or hydrogel layer into which the antigen or analyte must diffuse prior to being detected. With the use of our SAM based biosensor surface, this can be accomplished without the diffusion step allowing vapor phase detection.

Work to gather further data on the properties of this new detection technology has been successful. Data has been gathered showing that the biosensor works in air, but extreme conditions must be met to demonstrate to the scientific community that a reaction which most feel is impossible has been accomplished. The biosensor surface has been shown to detect TNT in the vapor phase at the nanogram level.

This biosensor surface can have wide application. It is a method by which any active biomolecule can be closely and effectively coupled to a SPR detector. With the capability to immobilize antibodies and other active biomolecules in a stable SAM-like layer, the immunochemical reactions can be done and detected in vapor phase as well as the liquid phase. This opens sensitive, and selective detection of any compound for which an antibody is available, or can be produced in air or in liquids.

Applications include detection in the vapor phase of high explosives, accelerant in arson investigations, illicit drugs, biological species including airborne bacterial spores. This makes possible devices capable of detecting explosives in airports or in other security situations, or for the detection of biological weapons.

The system can also be adapted for detection of bacteria in body fluids or hospital spaces including ventilation shafts. Detectors for drugs in blood, or drug metabolites in breath or spitum are possible.

Although other methods are available for the immobilization of antibodies onto metal surfaces, all of these utilize a relatively thick layer of immobilization compounds. A thick mounting layer has the effect of separating the active biomolecule from the SPR surface, and therefore decreasing sensitivity.

The commercially available Pharmacia Biacorp SPR biosensor surface utilizes a hydrogel matrix in which antibodies are physically trapped. This produces an active surface with a thickness of several thousand angstroms. Analyte molecules are forced to diffuse into the hydrogel prior to reacting with the entrapped antibodies. Practically, this surface will only work in the liquid phase. Another variation involves the direct attachment of the antibodies onto the metallized surface. This has been shown to affect the tertiary structure of the antibodies, even to actual denaturization by the metal surface. A biosensor layer for SPR spectroscopy is also described by Morgan et al. (Morgan, H., Taylor, D. M., *Biosensors & Bioelectronics*, 7(1992) 405–410). This consists of a metallized surface with a biotin-streptavidin layer which "tethers" the antibody layer. This method also produces a thick mounting layer insulating the antibodies from the surface plasmon, and decreasing sensitivity.

Our method immobilizes the antibody, or active biomolecule close to the SPR surface therefore maximizing the sensitivity, as well as protecting the active biomolecule. This allows for rapid and very specific detection of compounds or analytes in air. All present biosensor technology involving SPRS appears to rely on a liquid or hydrogel layer into which the antigen or analyte must diffuse prior to being detected. With the use of the new SAM based biosensor surface, this can be accomplished without the diffusion step allowing vapor phase detection.

A miniaturized and highly portable biosensor of improved sensitivity and selectivity capable of detecting bacterial spores as well as chemical agents in air is now also possible. The biosensor in its final form is envisioned to comprise a small remote or hand held battery powered unit with a concentrator which will push the air sample across the biosensor component. Determination of a positive result would consist of either an easy to read display for the hand held version, or the information could be telemetered to a remote location. Bacterial spores and a chemical compound may be reliably detected with the biosensor, and two or more analyses may also be accomplished simultaneously.

Surface Plasmon Resonance (SPR) spectroscopy is a readily miniaturizable optical method sensitive to minute changes in thickness and in the index of refraction of organic layers immobilized onto a metallic surface. This method, at high resolution, is capable of detecting a difference in thickness of less than $10^{-9}$ meters (nanometer (nm) range) which makes it able to detect the addition of small molecules to the organic layer.

The instrumentation itself is simple, consisting of a metallized active surface optically coupled to a prism with a half cylinder or other shape, including an optical fiber, a polarized low powered light source, and a detector, coupled to an analysis element or a SPRS chip. The active surface, or biosensor component, may comprise a specially prepared substrate coated with a metallic layer around 50 nm thick. This can be overcoated with a reactive organic compound which forms a Self Assembled Monolayer (SAM). A final layer may include one or more monoclonal antibodies in different positions on the substrate. The antibodies can be reacted with the SAM which can act to covalently tether them to the active surface. Such a surface will be able to react with the specific antigens to the immobilized antibodies even in the gas phase. The capture of the specific antigen by the antibody layer can change the thickness and index of refraction of the surface which is detected by SPR spectroscopy. Detection of TNT, a compound with very low volatility, can take place in the gas phase with this method at an estimated 200 ppb in air, or even 78 ppb in air, without a preconcentration step. The method is also capable of working in the liquid phase. TNT can be detected in a buffer solution of water at 0.3 ppb. In contrast, trained dogs are able to detect some organic compounds at 5–27 ppb. By changing the antibodies tethered to the active surface, new analytes can be detected with the same specificity and similar sensitivity. Simultaneous detection of more than one analyte can be accomplished by optically interrogating different areas on the substrate.

An existing SPR instrument may be utilized to show that bacterial spores, with and without a dispersant compound, can be detected at low concentrations on a SPR active surface in air. Two different species of bacterial spores may be utilized to demonstrate selectivity. Antibodies on the surface may be used to demonstrate simultaneous determination of one of the spores, and of a chemical agent. Toluene may be used as a simulant for the chemical agent.

Applications include detection in the vapor phase of high explosives, accelerants in arson investigations, illicit drugs, biological species including bacterial spores, as well as any compound for which an antibody can be made. This makes possible devices capable of detecting explosives in airports or in other security situations, or for the detection of biological weapons.

The potential commercial opportunities for a gas phase explosives detector are substantial. A rapid response, portable, low cost device would be of great interest for several potential customer groups. These include the airline industry, which presently spends large amounts of money on security, from on site personnel to detection devices. Devices that this particular industry has invested in to detect bombs and explosives include high cost immobile devices such as X-ray backscatter instrumentation, neutron activation, and an array of mass spectrometric devices. The device which we propose can also be used by security forces including police squads that find and deactivate bombs, customs agents for the detection of concealed drugs in shipping containers, and governments around the world for anti assassination security. This device also has the capability of unambiguously identifying the explosive or accelerant used in bombings or arson. The market for such a device is world wide.

This device would augment the existing efforts to find hidden explosives which currently employ trained dogs, special search personnel, camera surveillance, X-ray cameras for luggage, mass spectrometry devices with separate portable preconcentration devices, and in the case of non-metallic land mines, probing with hand held knives. The advantage of our device is that it can detect and analyze for explosives in a seconds-to-minutes time frame on the scene. This should substantially shorten the discovery to removal time period. This device can also eliminate the time lag in post blast or arson investigations, making this device a boon for the insurance industry.

With current trends, it is unlikely that terrorist bombing activities will slow and cease. Thus, the market opportunities for devices of this type should continue to grow for the foreseeable future. Many companies are competing in this market with a variety of devices ranging from portable gas chromatographic instrumentation to antibody-based sensors. For example, Barringer Technologies of New Jersey is developing Ion Mobility Specrometric devices, Science Applications International of San Diego, and various universities including Western Kentucky University, Bowling Green and even Oak Ridge National Laboratory have developed various instrumentation based on neutron or gamma ray analysis. The Naval Research Laboratory, in addition to the solution antibody based explosive detector discussed above, has also developed a nuclear quadruple resonance instrument now licensed to Quantum Magnetics (San Diego, Calif.). Other methods include photoacoustic spectroscopy (Jaycor, San Diego), Reversal Electron Attachment Detectors, (JPL, CA.), and Bofors Applied Technologies of the Netherlands who is developing an antibody-antigen device based on Guilbault's quartz crystal oscillator system, discussed above.

Of the aforementioned products, the only competition based on cost, and portability that should compete with our proposed device include dogs, and the Bofors Applied Technology device. Although the Guilbault technology using the quartz crystal oscillator is very sensitive, we believe that the ability for SPRS to detect differences in the antibody film thickness of only 4 angstroms should compete well. Further, the SPRS analysis, based on spectroscopic measurements, is quantitative, and instantaneous, and not affected by vibrational noise.

A non-limiting example of a typical gas phase explosives or accelerant detecting SPRS instrument can be made from an inexpensive HeNe laser, a polarizer, a small prism, and a rotatable stage. Alternatively, the device could be constructed using optical fibers 12 or using a CCD camera and a fixed prism. In either configuration, it is obvious that this can eventually be miniaturized into a hand held device, and attached to a slaved computer, or dedicated SPRS chip. With an attached preconcentration device, such a detector could be used to make rapid, specific, and sensitive determinations of the presence of explosives in air. At present this might primarily be for TNT, but other explosives could also be detected as antibodies for them become available. In principle, with a multiplexing detector, several antibody-antigen reactions could be detected at the same time, making detection of several explosives at once possible. We believe that this method will compete well with the above-mentioned methods because of its cost, portability, and its ability for fast in situ, detection.

The market for a SPR biosensor for a biological weapon such as anthrax spores is also considerable. The United States government is spending millions of dollars looking for a reliable field portable detector such as this to safeguard troops overseas, as well as to protect civilian targets against terrorist attack.

The foregoing discussion and the claims which follow describe the preferred embodiments of the present invention. Particularly with respect to the claims, it should be understood that changes and modifications may be made without departing from its essence and the broad aspects of the present invention. In this regard, it is intended that such changes and modifications would still fall within the scope of the present invention. It simply is not practical to describe and claim all possible revisions to the present invention which may be accomplished. All the various combinations and permutations of each of the claims should also be understood as disclosed through this application. To the extent such revisions utilize the essence of the present invention, each would naturally fall within the breadth of protection encompassed by this patent. This is particularly true for the present invention since its basic concepts and understandings are fundamental in nature and can be broadly applied.

The discussion included in this application is intended to serve as a basic description. The reader should be aware that the specific discussion may not explicitly describe all embodiments possible; many alternatives are implicit. The market place and manufacturing concerns may dictate the appropriate embodiments for the present invention. Particularly with respect to the discussion, it should be understood that a number of changes may be made without departing from the essence of the present invention. In this regard, it is intended that such changes—to the extent that they substantially achieve the same results in substantially the same way—will still fall within the scope of the present invention. It also may not fully explain the generic nature of the invention and may not explicitly show how each feature or element can actually be representative of a broader function or of a great variety of alternative or equivalent elements. Again, these are implicitly included in this disclosure. Where the invention is described in apparatus oriented terminology, each element of the apparatus implicitly performs a function. Apparatus discussions or claims may not only be included for the biosensor described, but also method or process claims may be included to address the functions the invention and each element performs. As but one example of this aspect, the disclosure of a "sensor" should be understood to encompass disclosure of the act of "sensing"—whether explicitly discussed or not—and, conversely, were there only disclosure of the act of "sensing", such a disclosure should be understood to encompass disclosure of a "sensor." Although the methods related to the system are being included in various detail, only an initial discussion directed toward the biosensor has been included. Naturally, that discussion could have some application to the various other methods and aspects discussed throughout the disclosure. Neither the description nor the terminology is intended to limit the scope of the claims which will be included in a full patent application.

Each of the various elements of the invention and claims may also be achieved in a variety of manners. This disclosure should be understood to encompass each such variation, be it a method or process embodiment of the biosensors, or even merely a variation of any element of these. Particularly, it should be understood that as the disclosure relates to elements of the invention, the words for each element may be expressed by equivalent terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all action may be expressed as a means for taking that action or as an element which causes that action. Similarly, each physical element or compositions disclosed should be understood to encompass a disclosure of the action which that physical element or composition facilitates.

In addition, it should be understood that, in the claims and in the application, the term "comprising" is meant to have an inclusive meaning rather than an exclusive one. It should be interpreted in its most expansive form so as to afford the applicant the broadest coverage legally permissible. Therefore, in countries, such as Australia, this term is not intended to have an exclusive, or more limited, meaning.

Any references mentioned in the application for this patent or cited in an information disclosure statement are hereby incorporated by reference, however, to the extent statements might be considered inconsistent with the patenting of this invention such statements are expressly not to be considered as made by the applicant.

We claim:

1. A method of detecting an explosive substance, comprising the steps of:
   a. obtaining a biosensor element made through the steps of:
      1) establishing a substrate which has a substrate surface;
      2) coating a bimetallic layer on said substrate surface;
      3) applying a tether layer on said bimetallic layer; and
      4) covalently binding a biosensor layer to said tether layer wherein said biosensor layer contains biomolecules specific for an explosive substance;
   b. applying said biosensor element to a surface plasmon resonance spectroscope having a prism to direct light;
   c. interrogating the surface of said biosensor element with a light source from said surface plasmon resonance spectroscope;
   d. exposing said biosensor element to an to an air sample in which said explosive substance might exist;
   e. interrogating again the surface of said biosensor element with said light source; and
   f. detecting a presence of said explosive substance with said surface plasmon resonance spectroscope.

2. A method of detecting an explosive substance as described in claim 1 wherein said substrate has a refractive index, wherein said prism has a refractive index, and wherein said step of applying said biosensor element to a surface plasmon resonance spectroscope comprises the step of matching the refractive index of said substrate with the refractive index of said prism of said surface plasmon resonance spectroscope.

3. A method of detecting an explosive substance as described in claim 2 wherein said step of establishing a substrate which has a substrate surface comprises the step of establishing a glass substrate.

4. A method of detecting an explosive substance as described in claim 2 wherein said step of establishing a substrate which has a substrate surface comprises the step of establishing a plastic substrate.

5. A method of detecting an explosive substance as described in claim 1 wherein said step of establishing a substrate which has a substrate surface comprises the step of establishing a substrate which has a silianized substrate surface.

6. A method of detecting an explosive substance as described in claim 1 wherein said step of coating a bimetallic layer comprises the step of coating a silver layer followed by a gold layer wherein said silver layer reacts with said gold layer to form an alloy layer.

7. A method of detecting an explosive substance as described in claim 6 wherein said step of coating a silver layer followed by a gold layer comprises the step of coating a silver layer followed by a gold layer to form an alloy layer which is about 50 nm thick.

8. A method of detecting an explosive substance as described in claim 1 wherein said step of applying a tether layer comprises the step of applying a self assembled monolayer.

9. A method of detecting an explosive substance as described in claim 8 wherein said step of applying a self assembled monolayer comprises the step of applying carboxylic acids of alkane thiols.

10. A method of detecting an explosive substance as described in claim 8 wherein said step of applying a self assembled monolayer comprises the step of applying alcohol derivatives of alkane thiols.

11. A method of detecting an explosive substance as described in claim 8 wherein said step of applying a self assembled monolayer comprises the step of applying an alkane thiol.

12. A method of detecting an explosive substance as described in claim 1 wherein said step of covalently binding a biosensor layer to said tether layer comprises the step of chemically immobilizing said biosensor layer.

13. A method of detecting an explosive substance as described in claim 12 wherein said step of covalently binding a biosensor layer to said tether layer comprises the step of covalently binding a layer of biomolecules to said tether layer wherein said biomolecules comprise protein fragments specific for said explosive substance, proteins specific for said explosive substance, antibody fragments specific for said explosive substance, or antibodies specific for said explosive substance.

14. A method of detecting an explosive substance as described in claim 13 wherein said step of covalently binding a biosensor layer to said tether layer comprises the step of covalently binding polyclonal antibodies to said tether layer.

15. A method of detecting an explosive substance as described in claim 13 wherein said step of covalently binding a biosensor layer to said tether layer comprises the step of covalently binding monoclonal antibodies to said tether layer.

16. A method of detecting an explosive substance as described in claim 15 wherein said step of covalently binding monoclonal antibodies to said tether layer comprises the step of covalently binding one species of monoclonal antibodies to said tether layer.

17. A method of detecting an explosive substance as described in claim 16 wherein said step of covalently binding one species of monoclonal antibodies to said tether layer comprises the step of covalently binding trinitrotoluene (TNT) monoclonal antibodies to said tether layer.

18. A method of detecting an explosive substance as described in claim 16 wherein said step of covalently binding one species of monoclonal antibodies to said tether layer comprises the step of covalently binding cyclotrimethylenetrinitramine (RDX) monoclonal antibodies to said tether layer.

19. A method of detecting an explosive substance as described in claim 1 wherein said step of exposing said biosensor element to an air sample in which said explosive sample might exist comprises the step of performing low volatility detection wherein said explosive substance has a concentration of less than or equal to about either 78 ppb or 200 ppb.

20. A method of detecting an explosive substance as described in claim 1 wherein said step of exposing said biosensor element to an air sample in which said explosive sample might exist comprises the step of concentrating said air sample prior to exposure of said air sample to said biosensor layer.

21. A method of detecting an explosive substance as described in claim 15 wherein said step of covalently binding monoclonal antibodies to said tether layer comprises the step of covalently binding a first monoclonal antibody species and a second monoclonal antibody species to said tether layer.

22. A method of detecting an explosive substance as described in claim 21 wherein said step of covalently binding a first monoclonal antibody species and a second monoclonal antibody species to said tether layer comprises the step of covalently binding said first monoclonal antibody species and said second monoclonal antibody species at different locations on said tether layer.

23. A method of detecting an explosive substance as described in claim 22 wherein said step of interrogating again the surface of said biosensor element with said light source comprises the step of optically interrogating different areas on the surface of said biosensor element.

24. A method of detecting an explosive substance as described in claim 23 wherein said step of optically interrogating different areas on the surface of said biosensor element comprises the step of detecting with said surface plasmon resonance spectroscope changes in thickness of said biosensor element at said different locations.

25. A method of detecting an explosive substance as described in claim 15 wherein said step of covalently binding monoclonal antibodies to said tether layer comprises the step of covalently binding multiple species of monoclonal antibodies to said tether layer.

26. A method of detecting an explosive substance as described in claim 25 wherein said step of covalently binding multiple species of monoclonal antibodies to said tether layer comprises the step of covalently binding each of said multiple species of monoclonal antibodies at a different location on said tether layer.

27. A method of detecting an explosive substance as described in claim 26 wherein said step of interrogating again the surface of said biosensor element with said light source comprises the step of optically interrogating different areas on the surface of said biosensor element.

28. A method of detecting an explosive substance as described in claim 21 wherein said step of optically interrogating different areas on the surface of said biosensor element comprises the step of detecting with said surface plasmon resonance spectroscope changes in thickness of said biosensor element at said different locations.

29. A method of detecting an explosive substance as described in claim 12 wherein said step of detecting a presence of said explosive substance with surface plasmon resonance spectroscope comprises the step of remotely detecting a presence of said explosive substance with said surface plasmon resonance spectroscope.

30. A method of detecting an explosive substance as described in claim 29 wherein said step of remotely detecting a presence of said explosive substance with said surface plasmon resonance spectroscope comprises the step of telemetering data obtained from the step of exposing said biosensor element to an environment in which said explosive substance might exist to a remote location at which said surface plasmon resonance spectroscope is available.

* * * * *